(12) United States Patent
Shin et al.

(10) Patent No.: US 7,713,173 B2
(45) Date of Patent: May 11, 2010

(54) EXERCISE MANAGEMENT FUNCTION PROVIDING SYSTEM AND METHOD

(75) Inventors: Jong-Pil Shin, Seoul (KR); Ki-Tae Lee, Seoul (KR); Sung-Pyo Yoon, Seongnam-si (KR); Jong-Hyun An, Seoul (KR)

(73) Assignee: Samsung Electronics Co., Ltd (KR)

( * ) Notice: Subject to any disclaimer, the term of this patent is extended or adjusted under 35 U.S.C. 154(b) by 279 days.

(21) Appl. No.: 11/582,722

(22) Filed: Oct. 17, 2006

(65) Prior Publication Data

US 2007/0123391 A1    May 31, 2007

(30) Foreign Application Priority Data

Nov. 28, 2005    (KR) .................... 10-2005-0114371

(51) Int. Cl.
*A63B 71/00*    (2006.01)
*A43B 5/00*    (2006.01)
*A61F 5/14*    (2006.01)

(52) U.S. Cl. ............... 482/8; 482/74; 36/114; 36/140

(58) Field of Classification Search .......... 482/1, 482/7, 8, 9, 52, 54, 74; 73/12.09, 379.04, 73/514.34, 768; 36/1, 113–116, 117.7, 118.5, 36/118.6, 147
See application file for complete search history.

(56) References Cited

U.S. PATENT DOCUMENTS

| | | | | |
|---|---|---|---|---|
| 4,534,365 A | * | 8/1985 | Bonetta et al. .......... 600/592 |
| 4,586,495 A | * | 5/1986 | Petrofsky ................ 602/2 |
| 4,703,445 A | * | 10/1987 | Dassler .................. 702/160 |
| 5,323,650 A | * | 6/1994 | Fullen et al. ............ 73/172 |
| 5,471,405 A | * | 11/1995 | Marsh .................... 702/41 |
| 5,661,916 A | * | 9/1997 | Huang ................... 36/132 |
| 5,815,954 A | * | 10/1998 | Huang ................... 36/132 |
| 5,925,001 A | * | 7/1999 | Hoyt et al. .............. 600/595 |
| 6,430,843 B1 | * | 8/2002 | Potter et al. ............ 36/29 |
| 6,967,904 B2 | * | 11/2005 | Wu et al. ................ 369/10 |
| 7,156,773 B2 | * | 1/2007 | Takai et al. ............. 482/7 |
| 7,169,084 B2 | * | 1/2007 | Tsuji .................... 482/8 |
| 7,421,369 B2 | * | 9/2008 | Clarkson ................ 702/150 |

(Continued)

FOREIGN PATENT DOCUMENTS

EP    1473655    *    3/2004

(Continued)

*Primary Examiner*—Loan H Thanh
*Assistant Examiner*—Sandhara M Ganesan
(74) *Attorney, Agent, or Firm*—The Farrell Law Firm, LLP

(57) ABSTRACT

An exercise management function providing system and method is disclosed having a shoe with built-in sensors for sensing a user's exercise. User exercise information is measured using sensor values from each of the sensors and the measured user exercise information is transmitted to a mobile terminal. Then, the mobile terminal receives the user exercise information so as to grasp a user's exercise state and quantity of motion, and provides an exercise management function in accordance with the user's exercise state and quantity of motion. Accordingly, the present invention provides an exercise program suitable for a user in accordance with a user's quantity of motion so that the user can get exercise suitable for a specific user, and the user can be provided with an exercise program to attain their own desired weight, thereby assisting with health care.

24 Claims, 6 Drawing Sheets

U.S. PATENT DOCUMENTS

| | | | | |
|---|---|---|---|---|
| 2001/0014938 A1* | 8/2001 | Bisinella | ...................... | 712/37 |
| 2004/0177531 A1* | 9/2004 | DiBenedetto et al. | ......... | 36/132 |
| 2004/0219498 A1* | 11/2004 | Davidson | .................... | 434/247 |
| 2005/0060906 A1* | 3/2005 | Zimerfeld | .................... | 36/3 R |
| 2005/0132617 A1* | 6/2005 | Potter et al. | .................... | 36/132 |
| 2005/0183292 A1* | 8/2005 | DiBenedetto et al. | ......... | 36/132 |
| 2005/0227811 A1* | 10/2005 | Shum et al. | .................... | 482/1 |
| 2007/0006489 A1* | 1/2007 | Case et al. | .................... | 36/132 |
| 2007/0054777 A1* | 3/2007 | Kawai et al. | .................... | 482/1 |
| 2007/0180737 A1* | 8/2007 | DiBenedetto et al. | ......... | 36/132 |
| 2007/0271826 A1* | 11/2007 | Mirza et al. | .................... | 36/132 |

FOREIGN PATENT DOCUMENTS

| | | |
|---|---|---|
| KR | 10-2001-0044501 | 6/2001 |
| KR | 1020010044452 | 6/2001 |
| KR | 1020020014005 | 2/2002 |
| KR | 10-2003-0004513 | 1/2003 |
| KR | 10-2004-0025328 | 3/2004 |

* cited by examiner

EXERCISE MANAGEMENT FUNCTION PROVIDING SYSTEM AND METHOD

PRIORITY

This application claims priority to an application entitled "Exercise Management Function Providing System and Method" filed with the Korean Intellectual Property Office on Nov. 28, 2005 and assigned Ser. No. 2005-114371, the contents of which are incorporated herein by reference.

BACKGROUND OF THE INVENTION

1. Field of the Invention

The present invention relates to an exercise management function providing system and method for managing a user's exercise.

2. Description of the Related Art

As society's interest in health increases, much importance has been recently attached to exercise for health care. Accordingly, the number of people intending to exercise has increased, and the people who intend to exercise desire to have the amount and state of their exercise managed so as to obtain exercise that is suitable for their own health states and body condition.

As a technique for measuring a conventional quantity of motion, there is a technique in which a device such as a step counter is built into a mobile terminal, and the number of the mobile terminal user's steps is counted so as to display the quantity of motion. According to such a technique of measuring the conventional quantity of motion, the mobile terminal has a built-in vibration sensor, senses the number of vibrations so as to measure the user's number of steps, and calculates the user's quantity of motion with respect thereto so as to display it.

However, where the number of steps is measured in such a manner using the vibration sensor built into the mobile terminal, there is a problem in that the measured number of steps will differ in accordance with what state a user keeps the mobile terminal, i.e. horizontal or vertical, making it difficult to measure an exact quantity of motion.

Further, conventional systems simply provide information only on the quantity of motion in accordance with the number of steps, and cannot ascertain the exercise state that the user exercises in. Furthermore, conventional systems do not provide an exercise program suitable for a user's quantity of motion, making it difficult to meet the user's needs and for the user to manage their own exercise state or quantity of motion.

SUMMARY OF THE INVENTION

Accordingly, the present invention has been made to solve the above-mentioned problems occurring in conventional systems, and it is an object of the present invention to provide an exercise management function providing system and method for providing a precise quantity of motion measurement result by linking a sports shoe with a mobile terminal.

It is another object of the present invention to provide an exercise management function providing system and method for ascertaining a user's exercise state so as to allow a user to exercise in a suitable exercise state.

It is a still another object of the present invention to provide an exercise management function providing system and method for ascertaining a user's exercise state so as to provide an exercise program suitable for a user.

In order to accomplish these objects of the present invention, according to an aspect of the present invention, there is provided an exercise management function providing system, which includes a shoe having built-in sensors for sensing a user's exercise so as to measure user exercise information using sensor values from each of the sensors, and to transmit the measured user exercise information; and a mobile terminal for receiving the user exercise information so as to grasp a user's exercise state and quantity of motion, and providing an exercise management function in accordance with the user's exercise state and quantity of motion.

In order to accomplish these objects of the present invention, according to another aspect of the present invention, there is provided an exercise management function providing method, which includes a shoe with built-in sensors for sensing a user's exercise, measuring user exercise information to transmit it; and a mobile terminal receiving the user exercise information so as to grasp a user's exercise state and quantity of motion, and providing an exercise management function in accordance with the user's exercise state and quantity of motion.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
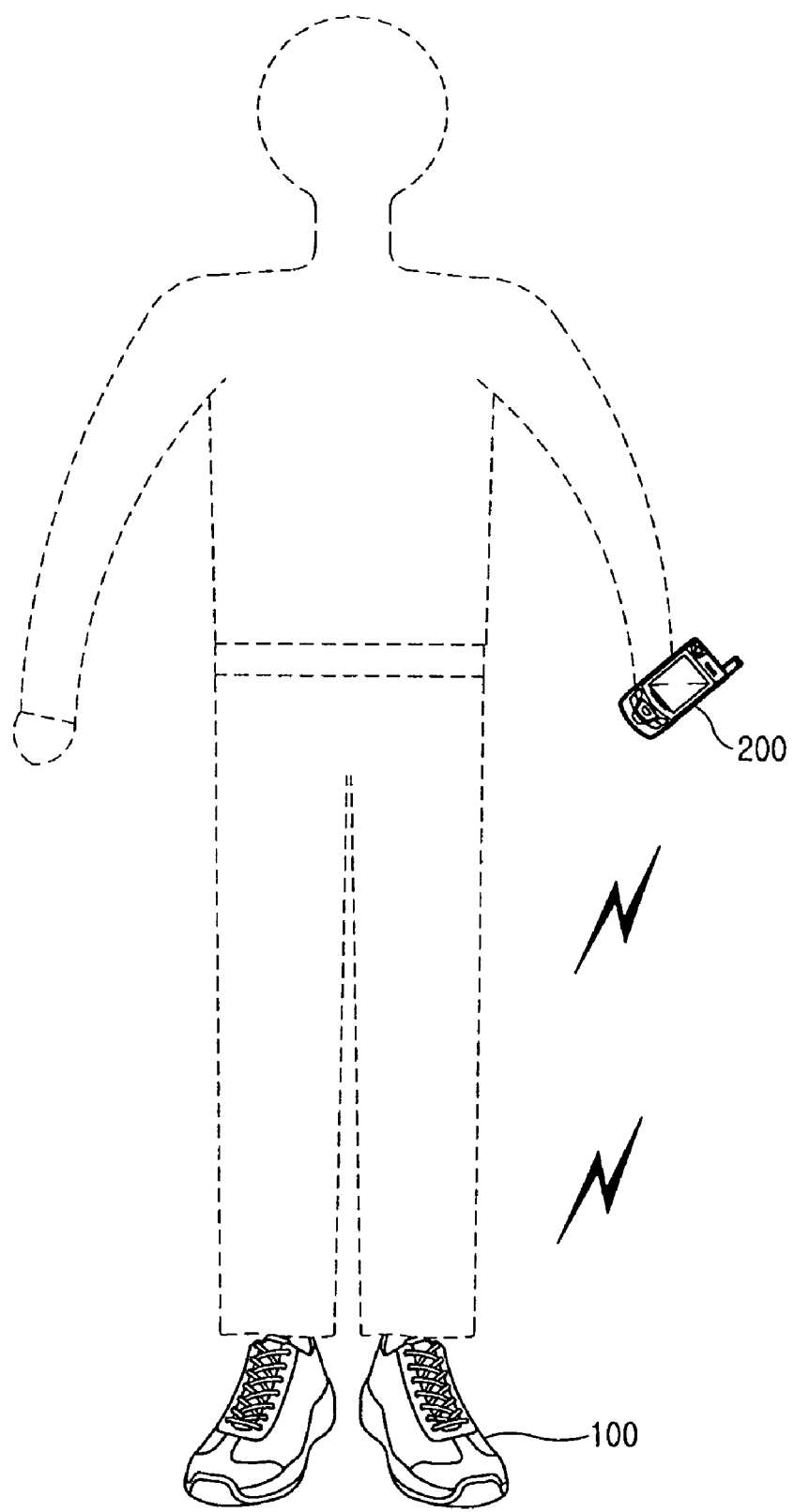
FIG. 1 illustrates an exercise management function providing system according to the present invention.

Hereinafter, preferred embodiments of the present invention will be described with reference to the accompanying drawings. In the following description, the same elements will be designated by the same reference numerals throughout the accompanying drawings. Further, in the following description of the present invention, a detailed description of known functions and configurations incorporated herein will be omitted when it may make the subject matter of the present invention rather unclear.

FIG. 1 illustrates an exercise management function providing system according to an embodiment of the present invention. Referring to FIG. 1, the exercise management function providing system, according to the embodiment of the present invention, includes a pair of intelligent sports shoes 100 and a mobile terminal 200.

The intelligent sports shoe 100 has built-in sensors for sensing user's exercise, and collects sensor data so as to measure user exercise information including the user's number of steps, elapsed exercise time, a mean exercise velocity, an exercise distance, a calorie consumption amount from exercise, body temperature in exercise, body state and the like. Further, the measured user exercise information is transmitted to the mobile terminal 200. The intelligent sports shoe 100, according to the embodiment of the present invention, is an example of a type of shoe, and may be applied to other types of shoes such as dress shoes and sandals, not only sports shoes.

The mobile terminal 200 may be a cellular phone, a Personal Digital Association (PDA) or the like. The mobile terminal 200 receives the user exercise information from the intelligent sports shoe 100, and ascertains a user's exercise state and quantity of motion using the user exercise information. Further, the mobile terminal 200 provides an exercise management function in accordance with the user's exercise state and quantity of motion. Here, the exercise management function includes functions of adjusting the internal structure of the intelligent sports shoe 100 depending on the user's exercise state, indicating the quantity of motion in a certain period of time, and providing an exercise program suitable for the user depending on the user's quantity of motion.

At this time, a process of measuring the user exercise information using the sensor data may be performed in the mobile terminal 200. Where the mobile terminal 200 measures the user exercise information, the intelligent sports shoe 100 transmits the sensor data collected during the user's exercise to the mobile terminal 200, and the mobile terminal 200 measures the user exercise information from the intelligent sports shoe using the sensor data.

A configuration of the intelligent sports shoe 100 and the mobile terminal 200 in the exercise management function providing system, according to the present invention, will be described in detail below.

Figure 2:
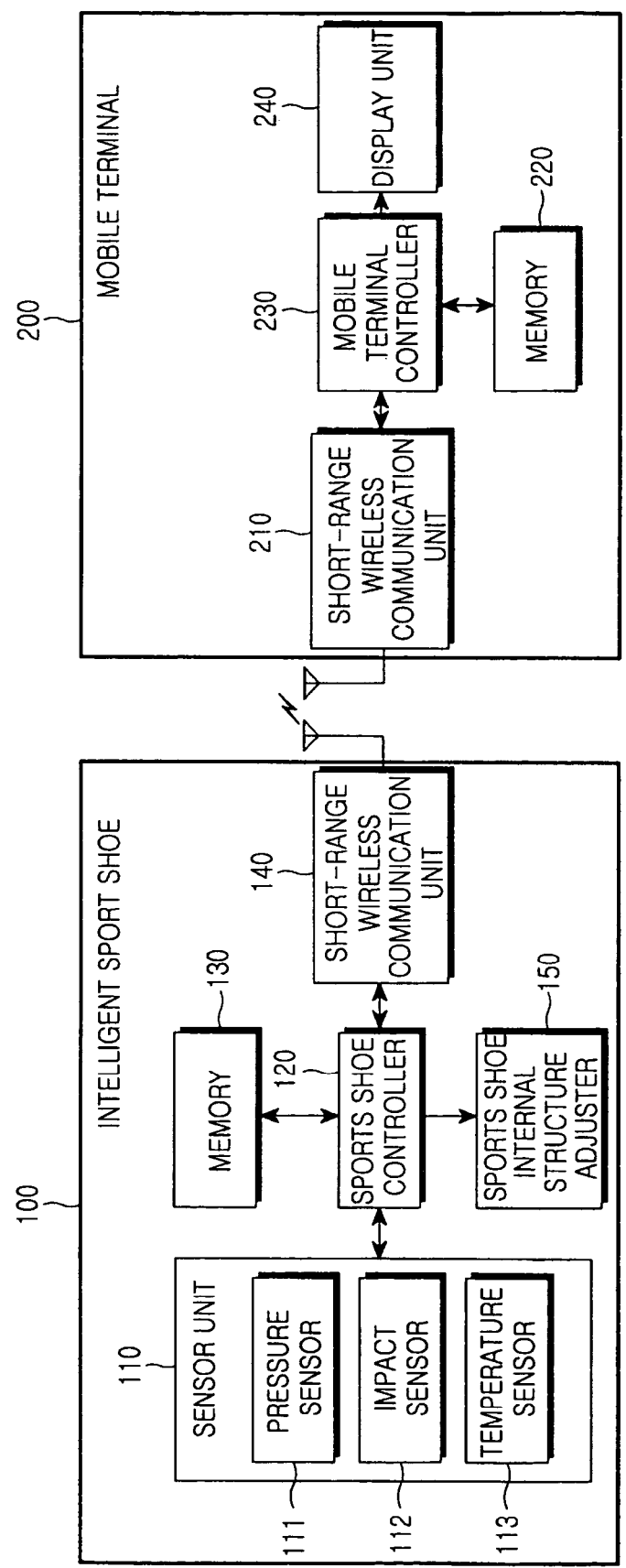
FIG. 2 is a block diagram showing components of the exercise management function providing system according to the present invention.

The intelligent shoe 100 will be discussed first. FIG. 2 is a block diagram showing components of the exercise management function providing system according to an embodiment of the present invention. Referring to FIG. 2, the intelligent sports shoe 100 includes a sensor unit 110, a sports shoe controller 120, a memory 130, a short-range wireless communication unit 140 and a sports shoe internal structure adjuster 150.

The sensor unit 110 includes a pressure sensor 111, an impact sensor 112 and a temperature sensor 113, and each of the sensors output a sensor value in accordance with the user's exercise.

The pressure sensor 111 senses pressure applied by a user's foot, and outputs a sensor value corresponding to the pressure sensing result. The impact sensor 112 senses impact applied by the user's foot, and outputs a sensor value corresponding to the impact sensing result. The temperature sensor 113 outputs a sensor value corresponding to a user temperature taken from the user's foot.

The sports shoe controller 120 may be configured as a microprocessor or the like. Further, the sports shoe controller 120 collects each sensor value of the sensor unit 110, and measures user exercise information using each of the selected sensor values.

The user exercise information includes the user's number of steps, elapsed exercise time, exercise distance, mean exercise velocity, calorie consumption amount, body temperature, body state and the like. For example, the user's number of steps refers to the number of times the user steps, and may be measured in accordance with a change in pressure and impact sensor value due to taking a step. Further, the elapsed exercise time refers to a duration of time that the user exercises, and may be measured in accordance with the time from when the user starts exercising to the time the user stops. The exercise distance refers to a distance over which the user exercises, and may be measured in accordance with the number of steps. The mean exercise velocity may be measured in accordance with the user's amount of exercise distance per hour or minute. The calorie consumption amount for exercise may be measured in accordance with a calorie amount consumed when the user exercises. The body temperature refers to a user's body temperature, and may be measured in accordance with a temperature sensor value. The body state refers to a state of balance of the user's body, such as whether it leans to the front, the rear, the left or the right when the user exercises. The pressure and impact sensors are arranged at various positions in the sole, and the balance state of the body may be measured in accordance with the difference of sensor values respectively output from the sensors. Further, the body state may also allow the balance state of the body to be measured utilizing the positioning of both feet via the pressure and impact sensors in each sole of the pair of intelligent sports shoes.

As described above, the sports shoe controller 120 measures user exercise information, and transmits the measured user exercise information to the mobile terminal 200 through the short-range wireless communication unit 140. At this time, the sports shoe controller 120 may collect sensor values in accordance with the user's exercise so as to transmit the user exercise information to the mobile terminal 200.

The memory 130 temporarily stores sensor values in accordance with the user's exercise, stores a program for measuring the user exercise information from each of the sensor values and data, and stores a program for transmitting the user exercise information to the mobile terminal 200.

The short-range wireless communication unit 140 may include an infrared communication module, a ZIGBEE® wireless communication scheme communication module, a BLUETOOTH® wireless communication scheme communication module and the like, and performs short-range wireless communications with the mobile terminal 200. ZIGBEE® and BLUETOOTH®, as used herein, each refer to specifications for suites of communication protocols for Wireless Personal Area Networks (WPANs). Such a short-range wireless communication unit 140 transmits user exercise information or sensor values in accordance with the user's exercise to the mobile terminal 200 under the control of the sports shoe controller 120.

The sports shoe internal structure adjuster 150 adjusts a sports shoe's internal structure under the control of the sports shoe controller 120. For example, the sports shoe internal structure adjuster 150 adjusts the thickness, height or the like of the cushioning and padding of the intelligent shoe 100 to a specific thickness or height, or adjusts the internal temperature of the intelligent shoe 100 under the control of the sport shoe controller 120. At this time, the sports shoe controller 120 receives sports shoe internal structure adjustment information provided in accordance with the current exercise state from the mobile terminal 200 so that it can control the internal structure of the intelligent sports shoe 100 to be adjusted.

Figure 3A:
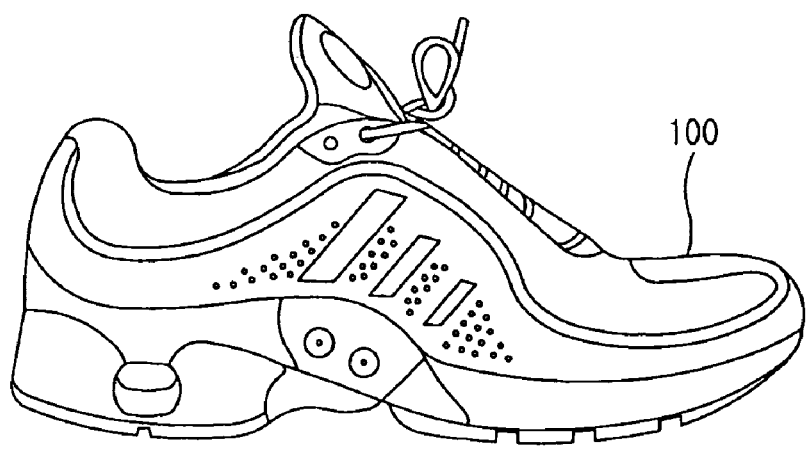
FIGS. 3A-C show a sports shoe and sole portion of the exercise management function providing system according to the present invention.
Figure 3B:
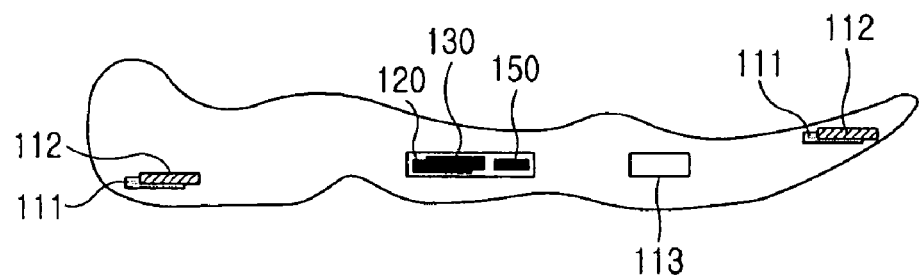
Figure 3C:
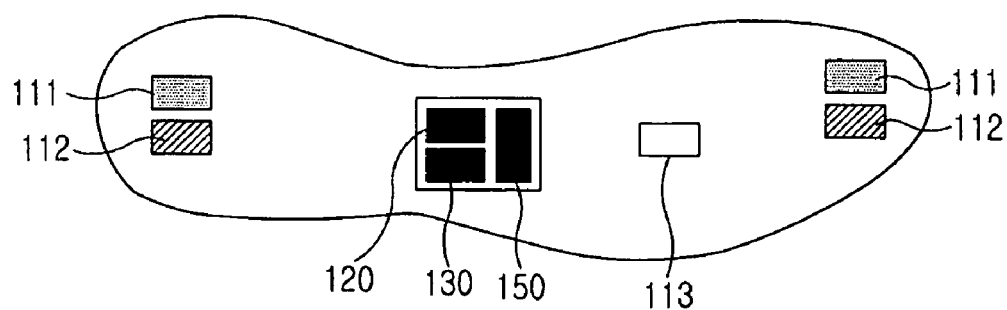

An example of the intelligent shoe 100 configured as described above is illustrated in FIG. 3. Referring now to FIGS. 3A-C. FIG. 3A is a side view of the intelligent sports shoe 100 according to the present invention, FIG. 3B is a side sectional view of the intelligent sports shoe 100 according to the present invention, and FIG. 3C is a plan view showing a cut-away bottom surface of the intelligent sports shoe 100 according to the present invention.

Referring to FIG. 3A-B, the sensors 111 to 113, the controller 120, the memory 130 and the short-range wireless communication unit 140 (not shown in FIGS. 3A-C) of the intelligent sports shoe 100, according to the embodiment of the present invention, may be positioned on a bottom portion or sole thereof.

Further, referring to FIG. 3C, the pressure and impact sensors 111 and 112 may be positioned at positions corresponding to the toe and heel of the sports shoe bottom such that the pressure and impact of a foot can be precisely sensed. Furthermore, the temperature sensor 113 may be positioned at a position where a user's temperature can be precisely sensed. In addition, the controller 120, the memory 130 and the short-range communication unit 140 may be positioned at a portion between the heel and center of a sole, to which the influence of pressure and impact is least applied by the foot.

Meanwhile, referring back to FIG. 2, the mobile terminal 200 includes a short-range wireless communication unit 210, a memory 220, a mobile terminal controller 230 and a display unit 240.

The short-range wireless communication unit 210 may include an infrared communication module, a ZIGBEE® wireless communication scheme communication module, a BLUETOOTH® wireless communication scheme communication module and the like, and performs short-range wireless communications with the short-range wireless communication unit 140 of the intelligent sports shoe 100. Such a short-range wireless communication unit 210 receives sensor values through user exercise from the intelligent sports shoe 100 or user exercise information measured using each of the sensor values.

The memory 220 stores user exercise information received from the intelligent sports shoe 100, ascertains a user's exercise state from the user exercise information, and stores information for calculating a quantity of motion. Further, the memory 220 stores sports shoe internal structure information in accordance with an exercise state, and stores exercise program configuration information for configuring an exercise program suitable for a user from the user exercise information.

The mobile terminal controller 230 ascertains the user's exercise state and quantity of exercise using the user exercise information received from the intelligent sports shoe 100, and provides an exercise management function in accordance with the user's exercise state and quantity of exercise.

For example, the mobile terminal controller 230 provides internal structure adjustment information of the intelligent sports shoe 100 in accordance with the user's exercise state to the intelligent sports shoe 100 so as to control the intelligent sports shoe 100 to adjust the cushioning, padding or internal temperature thereof. Further, the mobile terminal controller 230 ascertains a user's quantity of exercise over a certain period of time, and controls the display unit 240 to display the user's quantity of exercise for a certain period of time. Furthermore, the mobile terminal controller 230 configures an exercise program suitable for the user in accordance with the user's quantity of exercise, and controls the display unit 240 to display the exercise program.

The display unit 240 may includes a Liquid Crystal Display (LCD) or the like. The display unit 240 displays a user's quantity of exercise or an exercise program suitable for the user for a certain period of time under the control of the mobile terminal controller 230.

Accordingly, the exercise management function providing system configured as described above, according to the embodiment of the present invention, adjusts the internal structure of the intelligent sports shoe 100 in accordance with a user's exercise state when the user exercises so that the user can have the feeling of wearing a comfortable sports shoe during their exercise. Further, the exercise management function providing system precisely displays a user's quantity of exercise so that the user can exercise while checking on the quantity of their exercise. Furthermore, the exercise management function providing system provides an exercise program suitable for the user in accordance with the user's quantity of exercise so that the user can obtain exercise that is suitable for and personalized to the user.

Figure 4:
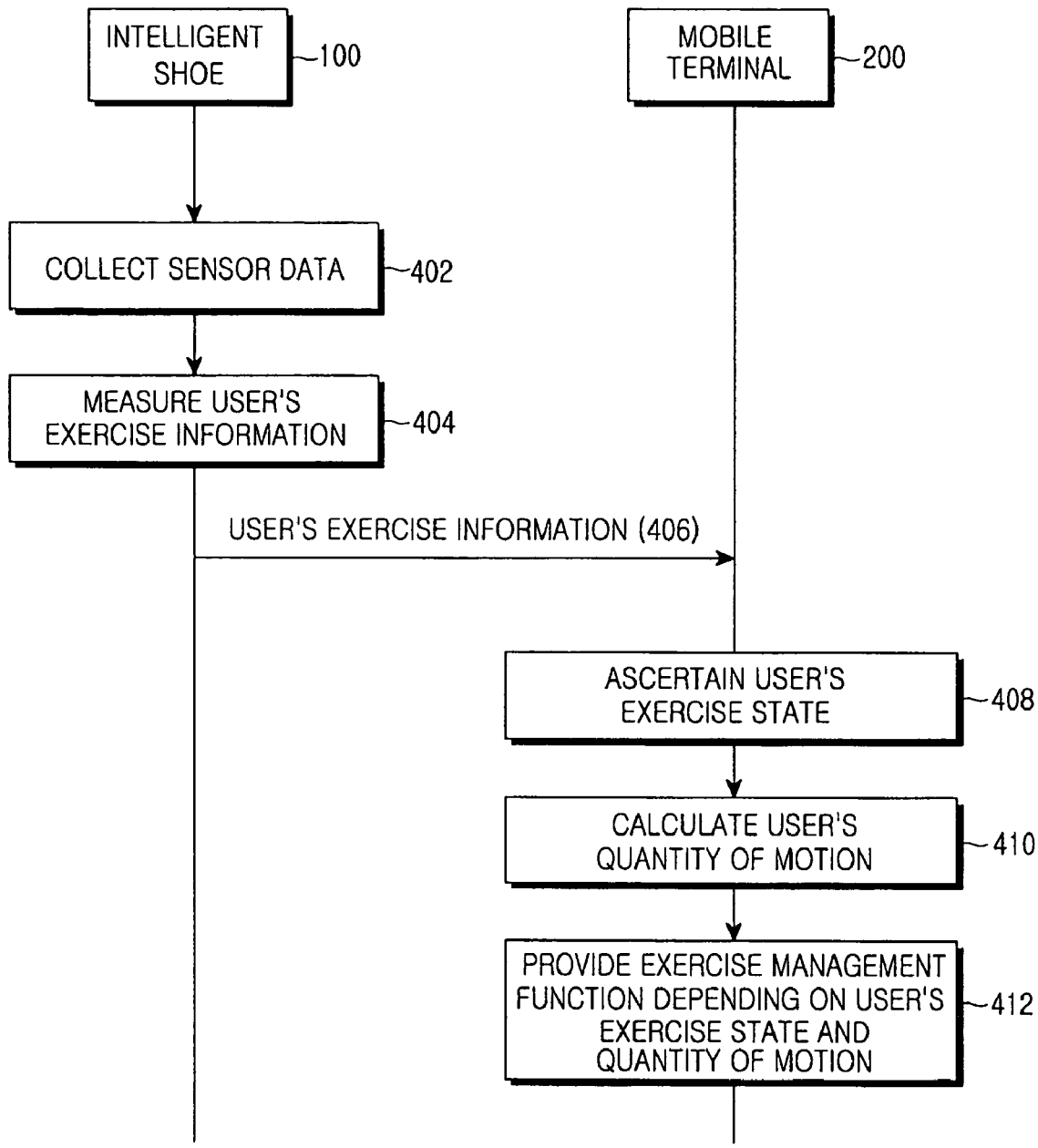
FIG. 4 is a flowchart illustrating an operation of an intelligent shoe and a mobile terminal in the exercise management function providing system according to the present invention.

An exercise management function providing method in the exercise management function providing system, according to the present invention, will be described in detail below. FIG. 4 is a flowchart illustrating an operation of an intelligent shoe and a mobile terminal in the exercise management function providing system according to the present invention.

Referring to FIG. 4, the intelligent sports shoe 100 collects sensor data through the user's exercise at step 402. The intelligent sports shoe 100 collects sensor data corresponding to pressure, impact and temperature sensor values by means of foot operation through the sensor unit 110.

Further, at step 404, the intelligent sports shoe 100 measures user exercise information using the respective collected sensor data. For example, the intelligent sports shoe 100 measures the user's number of steps, elapsed exercise time, exercise distance, mean exercise velocity, calorie consumption amount, body temperature, body state and the like using the pressure, impact and temperature sensor values.

At this time, the intelligent sports shoe 100 may measure the number of user's number of steps in accordance with a change in pressure and impact sensor values through the user's exercise. Further, the intelligent sports shoe 100 may measure the elapsed exercise time in accordance with the time from when the user starts exercising to the time the user stops exercising. Furthermore, the intelligent sports shoe 100 may measure the exercise distance in accordance with the number of user's steps. In addition, the intelligent sports shoe 100 may measure the mean exercise velocity in accordance with the user's amount of exercise distance per hour or minute. Moreover, the intelligent sports shoe 100 may measure the calorie consumption amount in accordance with predetermined calorie consumption amount information. Further, the intelligent sports shoe 100 may measure the user's temperature in accordance with a temperature sensor value. Furthermore, the intelligent sports shoe 100 may measure the state of balance of the body in accordance with the difference of sensor values respectively output from the sensors by respectively arranging the pressure and impact sensors at several positions of the foot, and may measure the balance state of the body by arranging the pressure and impact sensors on each of the left foot shoe and right foot shoe, and comparing sensor values of both feet.

If the user exercise information is measured, the intelligent sport shoe 100 transmits the user exercise information to the mobile terminal 200 using short-range wireless communication at step 406. At this time, the intelligent sports shoe 100 may use short-range wireless communication such as infrared communication, ZIGBEE® wireless communication scheme communication and BLUETOOTH® wireless communication scheme communication.

The mobile terminal 200 receives the user exercise information from the intelligent sports shoe 100, and determines a user's exercise state using the user exercise information at step 408. That is, the mobile terminal 200 determines the user's exercise state using information on the user's number of steps, elapsed exercise time, exercise distance, mean exercise velocity, calorie consumption amount, body temperature, body state and the like.

Further, the mobile terminal 200 calculates a user's quantity of motion at step 410. For example, the mobile terminal 200 calculates a user's quantity of motion using information on the user's number of steps, elapsed exercise time, exercise distance, mean exercise velocity, calorie consumption amount, body temperature, body state and the like. At this time, the user's quantity of motion may be calculated in calories (cal).

If the user's exercise state and quantity of motion are calculated, the mobile terminal 200 provides an exercise management function in accordance with the user's exercise state and quantity of motion at step 412. For example, the mobile terminal 200 provides internal structure adjustment information to the intelligent sports shoe 100 in accordance with the user's exercise state, so that the intelligent sports shoe 100 can adjust cushioning, padding or internal temperature. Further, the mobile terminal 200 ascertains a user's quantity of motion over a certain period of time, and displays the user's quantity of motion over a certain period of time. Furthermore, the mobile terminal 200 configures an exercise program suitable for the user in accordance with the user's quantity of motion, and displays the exercise program.

Figure 5:
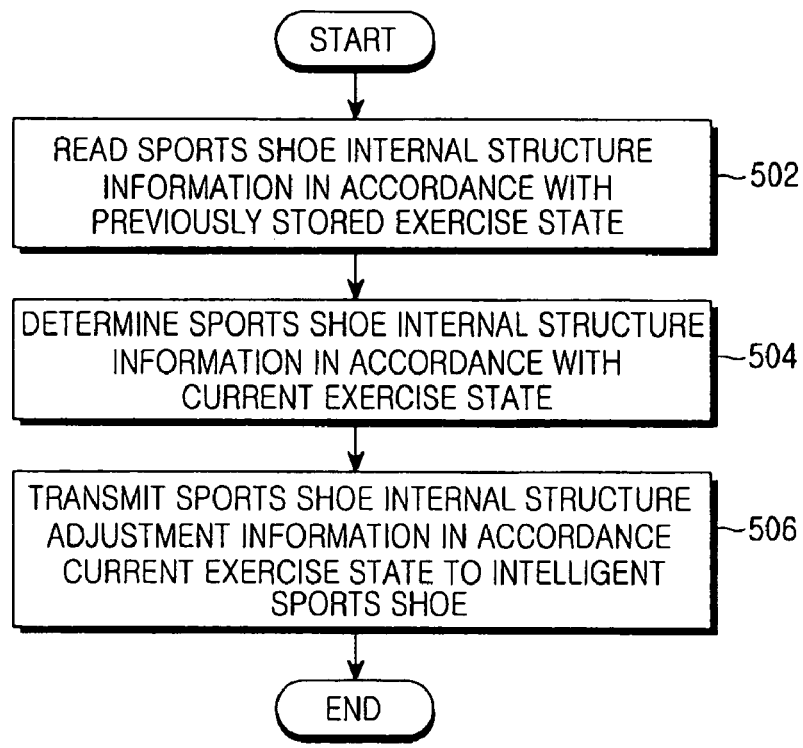
FIG. 5 is a flowchart illustrating a method of adjusting the internal structure of the sports shoe according to the present invention.

The function of adjusting the internal structure of the intelligent sports shoe 100 in accordance with a user's exercise state, among the exercise management functions of the mobile terminal 200, will now be discussed. FIG. 5 is a flowchart illustrating a method of adjusting the internal structure of the sports shoe according to the present invention.

Referring to FIG. 5, if a user's exercise state is ascertained, the mobile terminal 200 reads sports shoe internal structure information in accordance with a previously stored exercise state at step 502. The sports shoe internal structure information in accordance with the exercise state contains information on a sports shoe's cushioning, padding and temperature suitable for a user's body state and body temperature.

The mobile terminal 200 determines sports shoe internal structure information in accordance with the current exercise state using the previously stored sports shoe internal structure information at step 504. For example, the mobile terminal 200 determines information on a sports shoe's cushioning, padding and temperature in accordance with the user's current state of balance and body temperature.

Further, the mobile terminal 200 adjusts a sports shoe's internal structure in accordance with the current exercise state at step 506. For example, the mobile terminal 200 transmits information to the intelligent sports shoe 100 for adjusting the thickness of a sports shoe's cushioning and padding, and internal temperature in accordance with the user's current state of balance and body temperature. Then, the intelligent sports shoe 100 adjusts the thickness, height or the like of the cushioning and padding, or adjusts the internal temperature in accordance with the sports shoe internal structure adjustment information from the mobile terminal 200.

Figure 6:
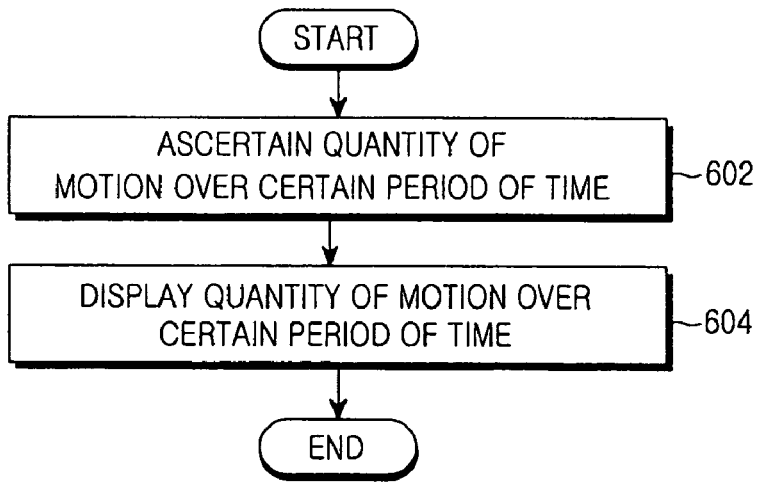
FIG. 6 is a flowchart illustrating a method of displaying a user's quantity of motion according to the present invention.

The function of indicating a quantity of motion for a certain period of time, among the exercise management functions of the mobile terminal 200, will now be discussed. FIG. 6 is a flowchart illustrating a method of displaying a user's quantity of motion according to the present invention.

Referring to FIG. 6, the mobile terminal ascertains a user's quantity of motion for a certain period of time at step 602. At this time, the mobile terminal 200 may ascertain the user's quantity of motion for a previously registered period of time, and ascertain the user's quantity of motion for a predetermined period (hour, day, month or year). Further, the mobile terminal 200 may determine the user's quantity of motion for a period of time, from when the user starts exercise until the time the user stops it.

Then, the mobile terminal 200 displays the user's quantity of motion over a certain period of time on the display unit 240 at step 604. At this time, the mobile terminal 200 may display the user's quantity of motion over a certain period of time as a graph or a numerical value. Further, the mobile terminal 200 may also display a variation of the user's quantity of motion, or whether the user's quantity of motion is decreasing or increasing.

Figure 7:
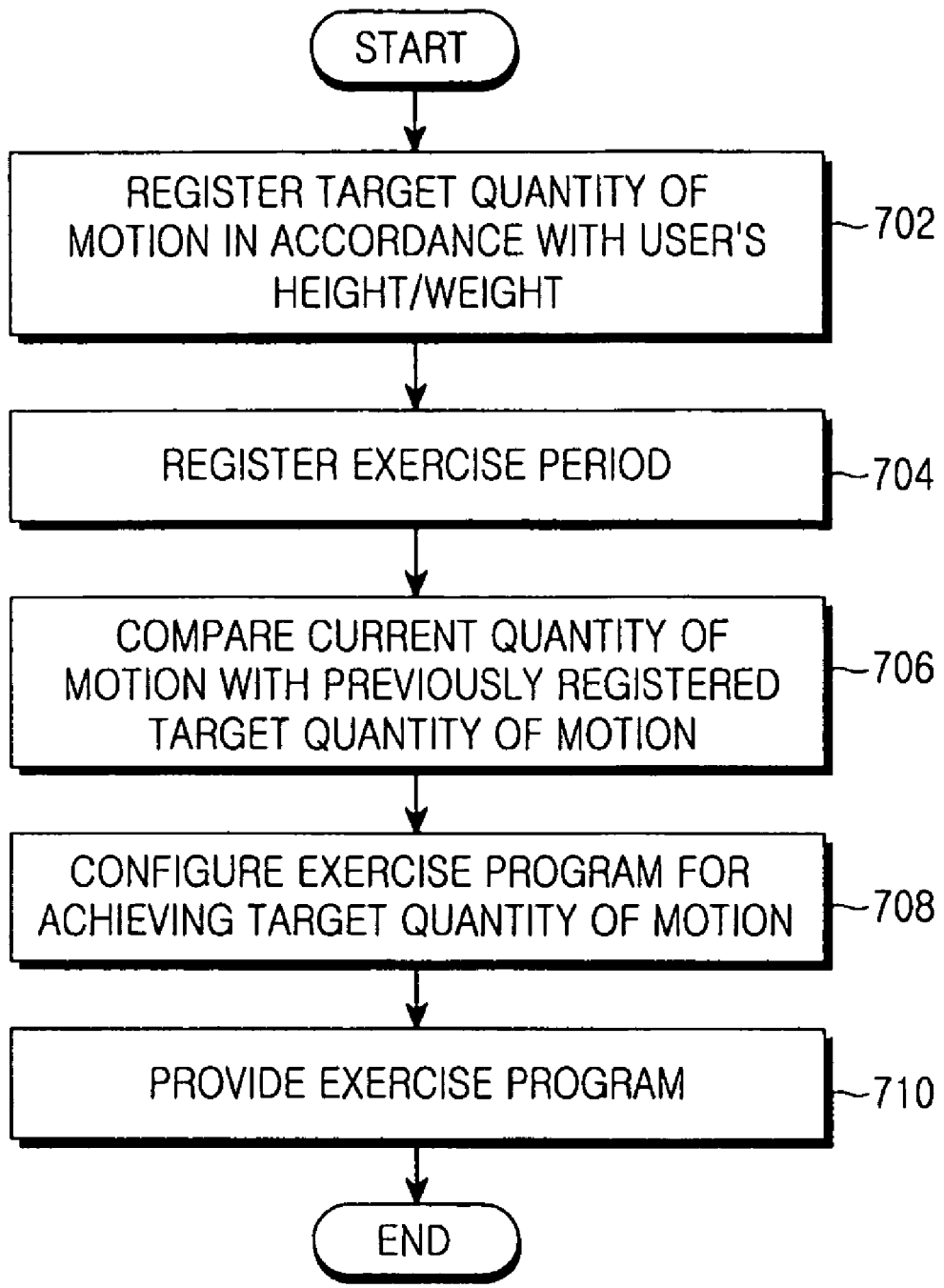
FIG. 7 is a flowchart illustrating a method of providing an exercise program according to the present invention.

Meanwhile, the function of providing an exercise program, among the exercise management functions of the mobile terminal 200, will now be discussed. FIG. 7 is a flowchart illustrating a method of providing an exercise program according to the present invention.

Referring to FIG. 7, the mobile terminal 200 registers a target quantity of motion in accordance with a user's height/weight at step 702. At this time, the mobile terminal 200 may previously store standard motion quantities depending on height/weight, and register the standard quantity of motion corresponding to the user's height/weight as the target quantity of motion. Further, the mobile terminal 200 may receive a user's desired weight as an input, and then register a quantity of motion required to attain the user's desired weight from the user's current height/weight as the target quantity of motion.

Then, the mobile terminal 200 registers an exercise period at step 704. That is, the mobile terminal 200 receives a period regarding how long the user will exercise in accordance with an exercise program, input from the user so as to register the period. At this time, the mobile terminal 200 may register a target exercise period by hour, day, month or year.

If the target quantity of motion and exercise period has been registered in such a manner, the mobile terminal 200 compares the current quantity of motion for the exercise period with the previously registered target quantity of motion at step 706. At this time the mobile terminal 200 compares the current quantity of motion with the previously registered target quantity of motion so as to determine whether the current quantity of motion is more or less than the previously registered target quantity of motion.

Further, at step 708, the mobile terminal 200 configures an exercise program for achieving the target quantity of motion. For example, the mobile terminal configures the exercise program such that the target quantity of motion is increased if the current quantity of motion is more than the previously registered target quantity of motion, and configures the exercise program such that the target quantity of motion decreases if the current quantity of motion is less than the previously registered target quantity of motion. At this time, the exercise program indicates what kind of exercise and how long the user should exercise and what kind of exercise to do.

If the exercise program is configured, the mobile terminal 200 provides the exercise program to the user at step 710. At this time, the mobile terminal 200 may display the exercise program on the display unit 240, and output it in a voice form.

As described above, the present invention adjusts a sports shoe internal structure in accordance with a user's exercise state when the user exercises so that the user can have the feeling of wearing a comfortable sports shoe during their exercise. Further, there is an advantage in that the present invention has sensors built therein, so that a user's quantity of motion can be precisely measured.

Furthermore, there is an advantage in that the present invention provides an exercise program suitable for a user in accordance with a user's quantity of motion so that the user can get exercise suitable for the particular user, and the user can be provided with an exercise program to attain their own desired weight, thereby assisting with weight control.

In addition, there is an advantage in that the present invention provides an exercise management function through a mobile terminal so that a mobile terminal utilization efficiency can be raised, and the mobile terminal can be applied as a device for use in health care.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. An exercise management function providing system, comprising:
   a shoe having built-in sensors for sensing a user's exercise so as to measure user exercise information using sensor values from the sensors, wherein the measured user exercise information is transmitted to a mobile terminal, and wherein at least one of the built-in sensors is a temperature sensor for measuring body temperature; and
   the mobile terminal for receiving the user exercise information so as to calculate a user's exercise state and quantity of motion, and providing at least one of a shoe internal structure adjustment function and a function of providing an exercise program for the user using the users's exercise state and quantity of motion,
   wherein the mobile terminal comprises:
   a short-range wireless communication unit for receiving user exercise information measured from the shoe;
   a memory for storing information calculating the quantity of motion, shoe internal structure adjustment information for adjusting an internal structure of the shoe in accordance with an exercise state and exercise program configuration information;
   a controller for calculating the user's exercise state and quantity of motion using the user exercise information, and providing, to the shoe, the shoe internal structure adjustment information in accordance with the calculated exercise state for providing the shoe internal structure adjustment function; and
   a display unit for displaying the exercise program in accordance with the calculated quantity of motion through the function of providing the exercise program under the control of the controller.

2. The system as claimed in claim 1, wherein the shoe is an intelligent sports shoe.

3. The system as claimed in claim 2, wherein the intelligent sports shoe comprises:
   a sensor unit for sensing pressure, impact and body temperature, which are transmitted from a foot during user's exercise;
   a controller for collecting each sensor value through the sensor unit to measure user exercise information; and
   a short-range wireless communication unit for transmitting the measured user exercise information to the mobile terminal through short-range wireless communication.

4. The system as claimed in claim 3, further comprising a memory for storing a program and data for measuring the user exercise information from the sensor values in accordance with the user's exercise.

5. The system as claimed in claim 3, wherein the sensor unit comprises:
   a pressure sensor for sensing pressure applied by the foot of the user to output a sensor value corresponding to the pressure sensing result;
   an impact sensor for sensing impact applied by the user's foot so as to output a sensor value corresponding to the impact sensing result; and
   a temperature sensor for outputting a sensor value corresponding to a body temperature of the user transmitted through the user's foot.

6. The system as claimed in claim 3, wherein the short-range wireless communication unit performs short-range wireless communications with the mobile terminal in any one communication scheme of infrared communication, ZIGBEE® wireless communication scheme communication and BLUETOOTH® wireless communication scheme communication.

7. The system as claimed in claim 3, wherein the user exercise information contains the user's number of steps, elapsed exercise time, exercise distance, mean exercise velocity, calorie consumption amount, body temperature, and body state.

8. The system as claimed in claim 1, wherein the shoe further comprises a sports shoe internal structure adjuster for adjusting the internal structure of the shoe in accordance with the shoe internal structure adjustment information.

9. The system as claimed in claim 1, wherein the shoe internal structure adjustment information contains information for adjusting the thickness and height of the cushioning and padding of the shoe and internal temperature adjustment information thereof.

10. The system as claimed in claim 1, wherein the controller ascertains the user's quantity of motion for a certain period of time, and causes the user's quantity of motion for a certain period of time to be displayed.

11. The system as claimed in claim 1, wherein the controller configures a user's exercise program in accordance with the user's quantity of motion, and selects an exercise program to be displayed.

12. An exercise management function providing method, comprising the steps of:
    sensing a user's exercise, measuring user exercise information, and transmitting the user exercise information by a shoe with built-in sensors; and
    receiving, by a mobile terminal, the user exercise information to calculate a user's exercise state and quantity of motion, providing at least one of a shoe internal structure adjustment function and a function of providing an exercise program for the user using the users's exercise state and quantity of motion, providing, to the shoe, shoe internal structure adjustment information in accordance with the calculated exercise state for adjusting an internal structure of the shoe through the shoe internal structure adjustment function, and displaying the exercise program in accordance with the calculated quantity of motion through the function of providing the exercise program,
    wherein measuring the user exercise information comprises sensing body temperature, which is transmitted from a foot during exercise, through at least one of the built-in sensors.

13. The method as claimed in claim 12, wherein the step of measuring the user exercise information comprises:
    sensing pressure and impact, which are transmitted from a foot during user exercise;
    measuring user exercise information in accordance with the pressure, impact and body temperature sensing result; and
    transmitting the measured user exercise information through short range wireless communication.

14. The method as claimed in claim 12, wherein the user exercise information contains a user's number of steps, elapsed exercise time, exercise distance, mean exercise velocity, calorie consumption amount, body temperature, and body state.

15. The method as claimed in claim 12, wherein the short-range wireless communication unit performs short-range wireless communications with the mobile terminal in any one communication scheme of infrared communication, ZIG-BEE® wireless communication scheme communication and BLUETOOTH® wireless communication scheme communication.

16. The method as claimed in claim 12, wherein the shoe is an intelligent sports shoe.

17. The method as claimed in claim 12, wherein the sports shoe internal structure adjustment information contains information for adjusting thickness and height of cushioning and padding of the intelligent sports shoe and internal temperature adjustment information thereof.

18. The method as claimed in claim 12, wherein the step of providing the exercise management function comprises ascending the user's quantity of motion over a certain period of time, and causing the user's quantity of motion for a certain period of time to be displayed.

19. The method as claimed in claim 12, wherein the step of providing the exercise management function comprises configuring a user's exercise program in accordance with the user's quantity of motion, and displaying the exercise program.

20. The method as claimed in claim 19, wherein the step of the mobile terminal configuring the exercise program comprises:
  registering a target quantity of motion in accordance with the user's height/weight;
  registering the user's exercise period;
  comparing the user's quantity of motion with the previously registered target quantity of motion; and
  configuring an exercise program for achieving the user's target quantity of motion as the comparison result of the quantity of motion.

21. The method as claimed in claim 20, wherein standard motion quantities in accordance with height/weight are previously stored, and the standard quantity of motion corresponding to the user's height/weight is registered as the target quantity of motion.

22. The method as claimed in claim 20, wherein, after a user's desired weight is input, a quantity of motion required to attain the user's desired weight from the user's current height/weight is registered as the target quantity of motion.

23. The method as claimed in claim 20, wherein the exercise period is registered by hour, day, month or year.

24. The method as claimed in claim 20, wherein the exercise program is configured such that the target quantity of motion increases if the current quantity of motion is more than a previously registered target quantity of motion, and the target quantity of motion decreases if the current quantity of motion is less than the previously registered target quantity of motion.

\* \* \* \* \*